(12) United States Patent
Turner

(10) Patent No.: US 11,376,412 B2
(45) Date of Patent: Jul. 5, 2022

(54) FLOW CONTROL SYSTEM

(71) Applicant: Spectrum Medical Ltd., Goucestershire (GB)

(72) Inventor: Stephen Turner, Gloucestershire (GB)

(73) Assignee: Spectrum Medical Ltd., Gloucester (GB)

( * ) Notice: Subject to any disclaimer, the term of this patent is extended or adjusted under 35 U.S.C. 154(b) by 190 days.

(21) Appl. No.: 16/080,565

(22) PCT Filed: Feb. 28, 2017

(86) PCT No.: PCT/GB2017/050535
§ 371 (c)(1),
(2) Date: Aug. 28, 2018

(87) PCT Pub. No.: WO2017/149290
PCT Pub. Date: Sep. 8, 2017

(65) Prior Publication Data
US 2019/0321621 A1    Oct. 24, 2019

(30) Foreign Application Priority Data
Mar. 1, 2016 (GB) .................... 1603536

(51) Int. Cl.
*A61M 39/28*    (2006.01)
(52) U.S. Cl.
CPC ........ *A61M 39/285* (2013.01); *A61M 39/281* (2013.01); *A61M 2205/3334* (2013.01); *A61M 2205/50* (2013.01)

(58) Field of Classification Search
CPC ................ A61M 39/286; A61M 39/28; A61M 5/16881; A61M 39/00; A61M 39/285;
(Continued)

(56) References Cited

U.S. PATENT DOCUMENTS 3,477,454 A   11/1969 Fields
4,682,755 A   7/1987 Bernstein
(Continued)

FOREIGN PATENT DOCUMENTS

CH           707421      6/2014
EP           0531137     3/1993
WO    WO2016/113545     7/2016

OTHER PUBLICATIONS

United Kingdom Intellectual Property Office, Search Report— Application No. GB 1603536.2, dated Aug. 3, 2016, 2 pages.
(Continued)

*Primary Examiner* — Jason E Flick
*Assistant Examiner* — Anna E Goldberg-Richmeier
(74) *Attorney, Agent, or Firm* — Sunstein LLP

(57) ABSTRACT

A clamping mechanism (30) for clamping a flexible tube comprises two rotatable bobbins (22, 32), each with a tube-engaging surface portion (24) defining boundaries of a free space through which a tube may extend. The shape of the tube-engaging surface portion (24) changes around the bobbin circumference, such that axial rotation of the bobbins (22, 32) reduces the free space and thereby squeezes the tube. This allows the flow through the tube to be altered dependent on the rotation of the bobbins.

9 Claims, 3 Drawing Sheets

(58) Field of Classification Search
CPC ............ A61M 39/281; A61M 5/16813; A61M 2205/3334; F16K 7/065; F16K 7/06
See application file for complete search history.

(56) References Cited

U.S. PATENT DOCUMENTS

| | | | |
|---|---|---|---|
| 5,549,458 A * | 8/1996 | Chapman | F04B 43/1253 417/360 |
| 6,957,798 B1 | 10/2005 | Schmidt | |
| 7,104,275 B2 * | 9/2006 | Dille | F16K 7/045 137/487.5 |
| 7,246,786 B1 | 7/2007 | Schmidt | |
| 2006/0042638 A1 * | 3/2006 | Niklewski | A61M 16/0051 128/207.18 |
| 2007/0051909 A1 | 3/2007 | Bernstein | |
| 2009/0125154 A1 * | 5/2009 | Yli-Koski | G05D 7/0635 700/282 |
| 2011/0314977 A1 | 12/2011 | Lewis | |
| 2012/0130299 A1 * | 5/2012 | Knott | A61M 1/3667 604/6.15 |
| 2015/0057816 A1 * | 2/2015 | Schick | G05D 7/0635 700/282 |
| 2017/0232182 A1 * | 8/2017 | Niimi | A61M 1/3666 604/66 |

OTHER PUBLICATIONS

European Patent Office, International Search Report and Written Opinion—Application No. PCT/GB2017/050535, 12 pages.

* cited by examiner

FLOW CONTROL SYSTEM

FIELD OF THE INVENTION

The present invention relates to a clamp for tubes. More specifically, the present invention relates to a clamping mechanism suitable to restrict the flow in tubes such as blood lines in a medical setting. The clamping mechanism may be used in clamping devices and in clamping methods.

BACKGROUND

In a medical setting, flexible tubes are typically used to transport fluids such as blood or solutions. A convenient way to restrict the flow without risking contamination by direct contact with a fluid is to squeeze a flexible tube using a clamp. Usual clamps are operated manually and releasable to remove the flow restriction on demand. Various mechanisms exist but in common they comprise tube-engaging elements that pinch or slide against an outer circumference of a flexible tube to squeeze the tube.

Using known clamps it is a challenge to set a flow rate at a particular restricted level below which flow is to be maintained. This is because flexible tubes of the type usually employed in medical settings may have to be squeezed to about half their original diameter before a noticeable effect on the flow rate is observed, and may have to be squeezed further to restrict the flow.

The present invention seeks to provide a more versatile clamping mechanism.

SUMMARY OF THE INVENTION

In accordance with a first aspect of the invention, there is disclosed a clamping mechanism for clamping a flexible tube to be provided as defined by claim 1.

The clamping mechanism comprises two rotatable bobbins, each bobbin comprising a tube-engaging surface portion, wherein the tube-engaging surface portions define boundaries of a free space between the bobbins through which a tube may extend, and wherein at least one tube-engaging surface portion has a shape that changes around at least part of a circumference of the bobbin, such that axial rotation of the bobbins reduces the free space to allow a tube provided in the free space to be squeezed by an amount dependent on the rotation of the bobbins, so as to deform a tube sufficiently to affect flow through the tube.

The tube-engaging surface portion is the part of the bobbins that comes into contact with a tube to be provided. It will be understood that the bobbins are installed side by side such that the tube-engaging surface portions may face each other. The surface portion may be a groove extending circumferentially around at least part of the circumference of a bobbin. A tube may be held between the tube-engaging surface portions, e.g., between the grooves, of two bobbins.

The tube to be provided is understood to be of a flexible nature, as used in clinical settings, and so can be reversibly squeezed by applying pressure to its outer surface. It is also implied that reduction of the outer pressure allows the tube to expand to its original diameter, or shape.

The shape of the tube-engaging surface portion changes, for instance, by way of the shape and/or radius of the bobbins at the surface portions increasing along at least part of the circumference of the bobbin. For instance, the depth of a circumferential groove may be tapered towards the bobbins axis, such that the groove becomes gradually less deep, or flatter, as it winds around the bobbin in one direction.

If a tube is held between two grooves of the bobbins, and the bobbins are rotated, it can be imagined how the tube is squeezed more the less deep the grooves are. As a groove is less deep (e.g., its radius increases), the free space between the grooves becomes smaller, and so the tube is held more tightly. This allows a fine degree of control over the amount of squeezing of the tube, because the bobbins may be rotated with high accuracy to gradually set a position with the shape for the required amount of squeezing.

The principle of using two bobbins to grip a tube is described in United Kingdom patent application number GB1500422.9 by the present applicant. In GB1500422.9, a dual-bobbins mechanism is employed to allow tubing of different diameter to be gripped and to be prevented from "walking" without risking undue squeezing, with an emphasis on avoiding an effect on the flow through the tubing. As such, the silhouette of the grooves of GB1500422.9 is shaped to avoid undue squeezing, for instance, by providing two grooves with semi-circular cross-section throughout which combine to provide a circular contact line for tube engagement. In GB1500422.9, even if too narrow a groove setting were used to grip a large tube, this would not affect flow through the tube, because—as set out above—a tube must be squeezed considerably before an effect on the flow rate becomes noticeable.

In contrast, the present invention employs a dual-bobbins mechanism to gradually squeeze a tube to increase a flow restriction, gradually, to allow the flow rate to be reduced and stopped. Thus, the mechanism described herein comprises a configuration wherein at least one tube-engaging surface portion comprises a shape suitable to deform a tube sufficiently to affect flow through the tube. More specifically, the configuration is suitable to affect the flow rate through the tube. In embodiments, the configuration is suitable to alter (i.e., to reduce or increase) the flow rate by at least 0.5 lpm. The configuration may allow the flow through a tube to be practically blocked.

A boundary may be defined as a contact line between a tube-engaging surface portion and a tube to be provided. The surface portions may comprise semi-circular grooves, such that two opposite grooves of equal diameter form a circular contact line to surround a tube of circular cross-section. If two bobbins are spaced apart, it will be understood that the contact lines may not be in contact with the full circumference of a tube to be provided. The silhouette of the tube-engaging surface portion may be other than round. The silhouette of the tube-engaging surface portions may be flat.

In embodiments, the silhouette of the tube-engaging surface portions changes gradually from semi-circular to rectilinear. One end of the tube-engaging surface portion may be semi-circular to accommodate a tube with minimal effect on the flow rate. One end of the tube-engaging surface portion may be rectilinear, or flattened, to squeeze a tube effectively to restrict and stop flow through the tube.

In embodiments, the clamping mechanism comprises a friction-reducing arrangement to reduce the grip of the bobbins as they deform the tube.

In embodiments, the clamping mechanism comprises a translatable carrier on which the bobbins are disposed to allow the bobbins to move along the tube as the bobbins are rotated.

The bobbins may be disposed on the translatable carrier to permit the bobbins to move along a tube as the bobbins rotate, or practically roll along the tube. An arrangement permitting the bobbins to roll along the tube may be regarded as a friction-reducing arrangement, because the rolling friction is lower than a sliding friction.

When a dual bobbins mechanism is used to restrict the flow in the absence of a friction-reducing arrangement, the grip of the tube-engaging surface portion to further restrict flow can potentially become so strong that rotation of the bobbins also pulls the tube along. Although a tube may be pulled only by a small distance, this would be undesirable in a clinical setting because it puts a strain on the connection of the tube. Also, the tube may be intended for connection into a patient and any movement of the tube is to be avoided.

The potential problem is schematically illustrated in FIGS. 1 to 3. In FIG. 1, a tube 10 is connected to a target 12 (the target 12 may be a venous reservoir) and to a source 14 via a connection 16. The source 14 may be a butterfly or venous cannula further connectable to a patient. A clamping mechanism 20 comprises a dual-bobbins mechanism comprising a first bobbin 22 and a second bobbin 32. The two bobbins are mounted on a common support 28. The support 28 is fixed in position and so the position of the bobbins 22 and 32 is not intended to change relative to the source 14 and the target 12.

The first bobbin 22 comprises a groove 24 constituting a tube-engaging surface portion. The depth of the groove 24 along the circumference of the bobbin 22 gradually decreases. The configuration of the second bobbin 32 is symmetrical to that of the first bobbin 22. The bobbins are arranged side-by-side on the common support 28 such that the grooves face each other to define a free space between the bobbins.

Cross-sectional FIG. 2A illustrates the tube 10 extending through the free space between the grooves 24 of the bobbins 22 and 32. In FIG. 2A, two bobbins 22 and 32 are shown in an orientation in which two semi-circular portions of the grooves 24 face each other to define an approximately circular free space between them. In the free space, a tube 10 having a circular cross-section is held in a non-squeezed condition 10A. Turning to FIG. 2B, the two bobbins 22 and 32 of FIG. 2A are rotated to an orientation in which the shape of the grooves 24 is altered relative to the FIG. 2A orientation. In the FIG. 2B orientation, both grooves 24 are flatter, and the free space between the grooves 24 is correspondingly reduced (more oval). Thus, the tube 10 is squeezed to a condition 10B. By sufficiently squeezing the tube 10, the flow rate through it can be affected.

In FIGS. 1 and 3, the first bobbin 22 comprises a marker 26 merely for illustration purposes, to better visualise a rotation of the first bobbin between Figures. The marker 26 is not necessarily present in an actual embodiment.

In FIG. 3, the first bobbin 22 and the second bobbin 32 are counter-rotated relative to the FIG. 1 position. This is also indicated by the marker 26 at a different orientation. The counter-rotation is indicated by a first arrow 34 for the first bobbin 22 and by a second arrow 36 for the second bobbin 32. Because the depth of the grooves along the circumference of the bobbins gradually decreases (e.g., from a semi-circular silhouette, as shown in FIG. 2A, to a flatter silhouette, as shown in FIG. 2B), by way of the counter-rotation, the free space defined by the boundaries of the grooves 24 is reduced relative to the FIG. 1 orientation.

Thereby, the tube 10 is gripped more tightly and squeezed. As the bobbins are fixed on the common support 28, the tight grip of the bobbins may cause the tube 10 to be pulled in the direction of the counter-rotation, as is indicated by arrow 18, away from the source 14. This puts a strain on the connection 16 and may even lead to the connection 16 detaching from the source 14, as indicated in FIG. 3.

Furthermore, the grip strength and ensuing tube-pulling effect may not be equal in both directions (i.e., in the direction of increasing a flow restriction and in the direction of reducing a flow restriction), such that repeatedly restricting and releasing a tube may lead to a significant cumulative tube transportation effect.

In contrast, by providing a mechanism that allows the bobbins to move along the frame as they rotate, the contact line of the tube-engaging portion moves along the tube as the bobbins roll along the tube. The bobbins may move along the frame in both directions along the tube. Thus, whether the bobbins are rotated to increase a flow restriction or to reduce it, their risk of pulling the tube in either direction is reduced, and can be considered practically eliminated.

In embodiments, the bobbins are configured to engage the tube in a synchronised manner.

The arrangement may consist of a mechanical coupling, or of control signals.

This helps to ensure that both bobbins are aligned relative to one another as they move along the frame, to ensure that a tube is effectively squeezed by the bobbins.

In embodiments, the clamping mechanism comprises a driver configured to effect synchronized rotation of both bobbins.

The driver may directly drive the bobbins. The driver may drive a common support on which the bobbins are disposed, such that driving the common support causes the bobbins to be moved simultaneously.

The driver may consist of a lead screw engaging a corresponding mechanism of the two bobbins. Actuation of the lead screw results in synchronized rotation of the bobbins. Furthermore, as lead screws can be actuated with high precision, for instance, using stepper motors with sub-micrometre precision, the degree of bobbin rotation, and thus the degree of flow restriction, can be controlled with high accuracy.

In embodiments, the clamping mechanism comprises a frame on which the carrier is translatable relative to the tube.

The frame allows a length of tube to be accommodated to ensure the bobbins can translate along the tube along their full travelling range without inhibition. This helps to ensure that the clamping mechanism is installed on a sufficiently long tube portion.

In embodiments, the clamping mechanism comprises a bobbin-frame coupling mechanism configured to couple rotation of a bobbin with a movement of the bobbin along the frame.

The bobbin-frame coupling mechanism may comprise, disposed in the frame, a toothed rack or a rack having a toothed portion. One or both bobbins may comprise a gear engaged with the toothed portion. Thus, if the driver acts directly on the bobbins to rotate them, rotation of a bobbin may result in a corresponding movement along the rack and, thus, the frame. Vice versa, if the driver acts on the carrier as it translates the bobbins along the rack, this may result in a corresponding rotation of the bobbin.

The coupling may be understood as a proportional movement. For instance, a particular amount of bobbin rotation may correspond to a travel distance along the frame proportional to the amount of bobbin rotation. Likewise, a particular speed of bobbin rotation may correspond to a travel speed along the frame, proportional to the speed of bobbin rotation.

This allows the movement of a bobbin along the frame to be effected upon rotation of a bobbin, or, vice versa, allows the rotation of a bobbin to be effected upon its movement along the frame. This helps to ensure that a bobbin rotates as it moves, such that the bobbins effectively roll along a tube.

In embodiments, the clamping mechanism comprises control logic that allows a position along the tube-engaging surface portion to be related to a flow rate through the tube.

In embodiments, the clamping mechanism comprises control logic that allows a degree of bobbin rotation to be related to a flow rate through the tube.

The relationship between the bobbin rotation, the amount of squeezing of a tube, and the ensuing degree of flow restriction is not necessarily linear. For instance, a tube may need to be squeezed to less than 50% of its original diameter before an effect on the flow rate becomes noticeable. Once a flow restriction is noticeable, minor pressure adjustments upon the tube may have disproportionately larger effects on the flow rate.

Furthermore, the relationship between bobbin rotation and flow rate depends on parameters such as the tube type and tube cross-section, and also on the geometry and shape of the tube-engaging surface portion (i.e., how much the free space changes as the bobbin is rotated), on the size and diameter of the bobbins, and other parameters. These parameters may determine a given setup.

For a given setup, it is possible to relate, or map, the flow rate to bobbin rotation. To provide an illustrative mapping, a bobbin rotation corresponding to a tube squeezing to between 100% to 40% of the original tube diameter may have no noticeable effect on the flow rate. A bobbin rotation corresponding to a tube squeezing to between 40% and 30% may restrict a flow rate to no more than 3.5 litres per minute (lpm), to between 30% and 20% to no more than 3 lpm, to between 20% and 10% to no more than 2 lpm, and to less than 10% may restrict the flow rate to no more than 1 lpm. Having established a mapping for a particular setup, the setting of a particular flow restriction is facilitated.

The flow rate restriction may be mapped to a degree of rotation of the bobbins, or to a position along the tube-engaging surface portion.

For instance, a control system as described in United Kingdom patent application number GB1520364.9 by the present applicant may be used to restrict the flow rate of a venous line into a venous reservoir from an unrestricted flow rate in the region of 4 to 5 lpm to "half" the unrestricted flow rate. Assuming an unrestricted flow rate of 4 lpm, a clinician or staff member may, thus, set the restriction to 2 lpm (half of 4 lpm) via a control input interface. The control logic may, in that case, interpret an input to set a flow restriction to a level of "2 lpm" and convert the input into an amount of bobbin rotation (or, by extension, to an amount of travel of a bobbin carriage or lead screw rotation), required to squeeze the tube until the flow restriction reaches 2 lpm, or, depending on the accuracy of the mapping, approximately 2 lpm. The control logic may rotate the bobbins according to the amount determined, and the ensuing flow rate can be assumed to be practically, or close to, 2 lpm.

The mapping functionality may be used in combination and/or to complement a closed-loop control mechanism.

Continuing from the above example, once the control logic has set a flow restriction of about 2 lpm, the control system may then proceed to use a closed-loop control mechanism, employing a flow sensor measuring the actual flow rate through the tube, to re-adjust the flow restriction if required to maintain the actual flow rate at no more than 2 lpm.

Setting an initial flow rate based on a mapping relation before switching to a closed-loop control reduces the risk of overshooting responses. Also, this helps to implement a particular flow restriction more quickly.

The control logic may be comprised in a processor and software instructions implemented by the processor to carry out the mapping functionality.

In embodiments, the clamping mechanism comprises a backup power source.

The clamping mechanism may be designed primarily for mains-powered operation. The backup power source allows the clamping mechanism to be powered independently of mains power. The backup power source is configured to provide sufficient power in the event of a power loss to carry out an emergency procedure. For instance, an emergency procedure may be the opening of any flow restrictions. Thus, the backup power source may have sufficient power to allow the bobbins to be rotated to the open position.

In embodiments, the clamping mechanism comprises a quick-release feature causing, upon its actuation, the bobbins to disengage the clamping mechanism.

The clamping mechanism may comprise a quick-release feature that permits the tube-engaging surface portions to disengage the tube. This may be achieved by disengaging a coupling mechanism, e.g., by decoupling a gear from a toothed rack, for instance by axially shifting the bobbin. The quick-release feature may be a mechanical button overriding electronic controls. Actuation of the quick-release feature may allow a user to quickly pull away a bobbin, in particular in a manner that permits subsequent reassembly without difficulty. This is to allow any flow-restrictions to be removed instantly, without having to navigate a standard user interface.

In embodiments, the clamping mechanism further comprises a flow sensor configured to determine a flow value indicative of the flow rate through the tube to be provided.

In embodiments, the clamping mechanism further comprises a controller configured to process the flow value, and to control the clamping mechanism to alter the flow restriction on the tube to maintain a flow rate that does not exceed a restriction threshold.

In accordance with a second aspect of the invention, there is disclosed a clamping mechanism for clamping a flexible tube to be provided as defined by claim 14.

The clamping mechanism comprises two rotatable bobbins, each bobbin comprising a tube-engaging surface portion, wherein the tube-engaging surface portions define boundaries of a free space between the bobbins through which a tube may extend, and wherein at least one tube-engaging surface portion has a shape that alters around at least part of a circumference of the bobbin, such that axial rotation of the bobbins alters the free space available for accommodating a tube, wherein the clamping mechanism comprises a translatable carrier on which the bobbins are disposed to allow the bobbins to move along the tube as the bobbins are rotated.

Any of the features and embodiments described in relation to the first aspect may be combined with the second aspect.

In accordance with a third aspect of the invention, there is disclosed a clamping mechanism for clamping a flexible tube to be provided as defined by claim 15.

The clamping mechanism comprises two rotatable bobbins, each bobbin comprising a tube-engaging surface portion, wherein the tube-engaging surface portions define boundaries of a free space between the bobbins through which a tube may extend, and wherein at least one tube-engaging surface portion has a shape that alters around at least part of a circumference of the bobbin, such that axial rotation of the bobbins alters the free space available to accommodate a tube, wherein the clamping mechanism comprises a quick-release feature causing upon its actuation the bobbins to disengage the clamping mechanism.

Any of the features and embodiments described in relation to the first aspect may be combined with the third aspect.

DESCRIPTION OF THE FIGURES

Exemplary embodiments of the invention will now be described with reference to the Figures, in which.

DESCRIPTION

Figure 1:
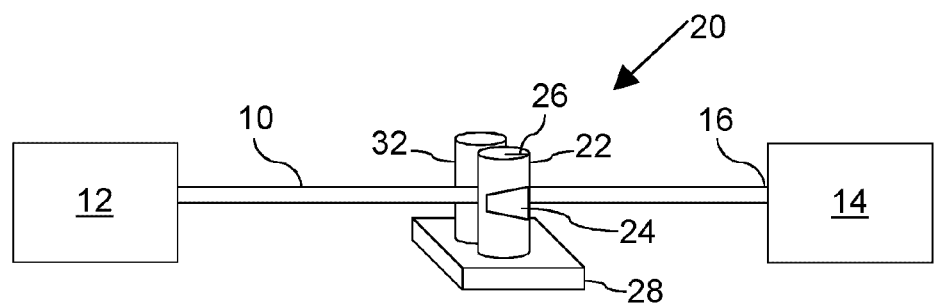
FIGS. 1 and 3 show steps of a sequence of a dual-bobbins tube-restricting mechanism to illustrate a potential problem addressed by embodiments described herein.
Figure 2A:
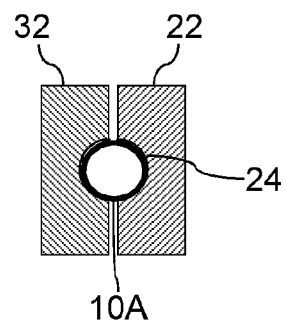
FIGS. 2A and 2B show cross-sections of two bobbins engaging a tube to illustrate the tube-restricting mechanism.
Figure 2B:
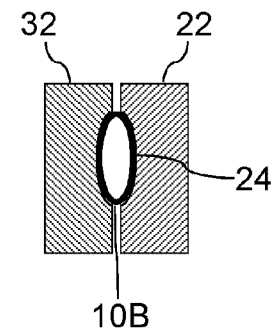
Figure 3:
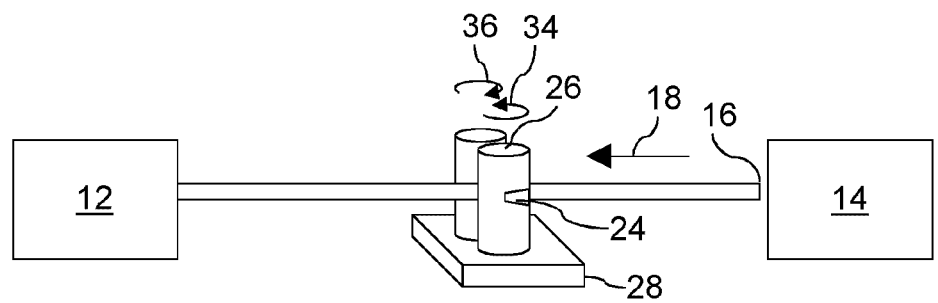
Figure 4:
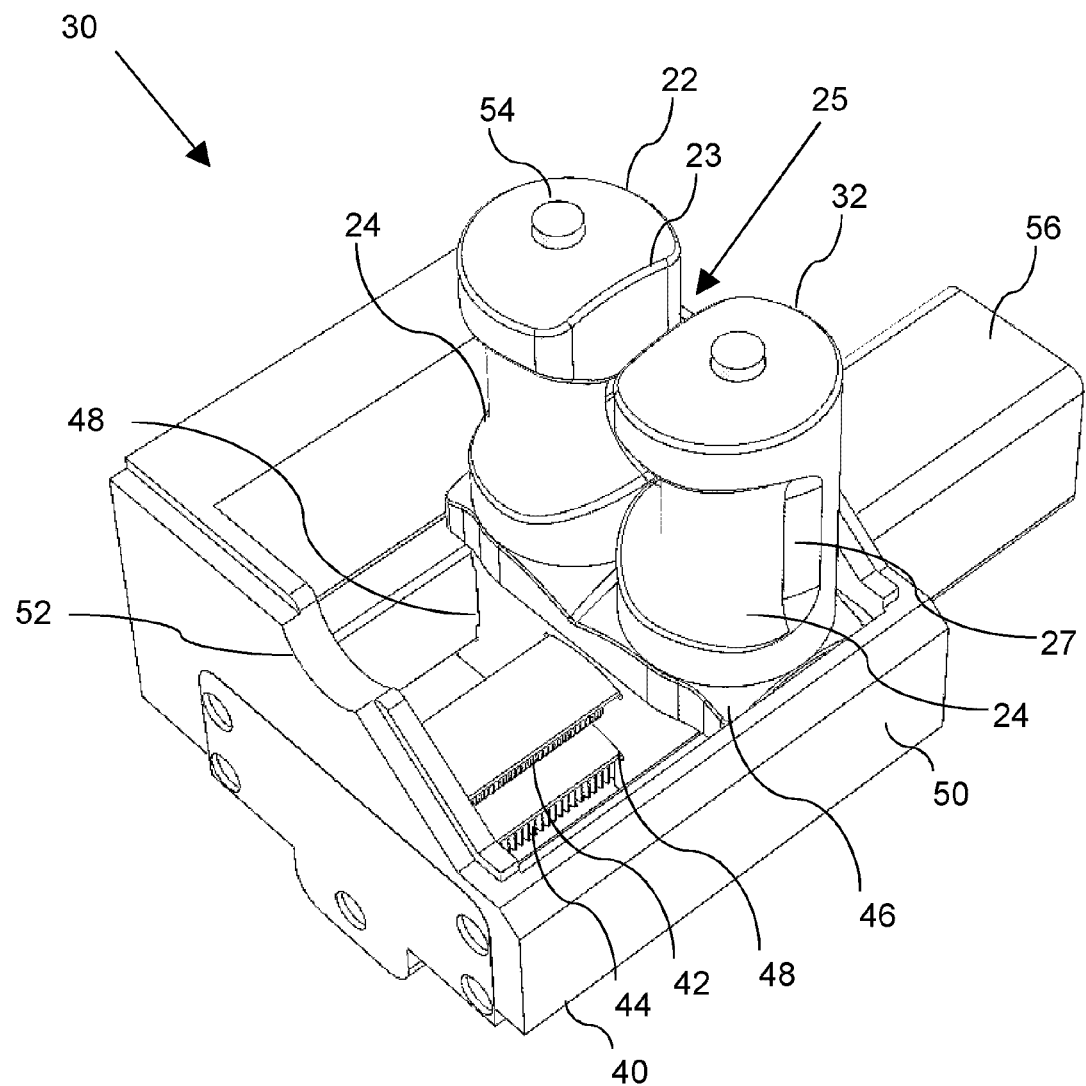
FIG. 4 shows a clamping mechanism in accordance with an exemplary embodiment of the invention.

FIGS. 1 to 3 have been described earlier in the present specification. Turning to FIG. 4, a clamping mechanism 30 comprises a first bobbin 22 and a second bobbin 32 which are disposed on a translatable carrier 46, translatable in a frame 40. The first bobbin 22 is generally cylindrical and comprises on its mantle surface a groove 24 constituting a tube-engaging surface portion. The groove 24 has a radius that increases, relative to the central axis of rotation of the first bobbin 22, along at least part of the circumference of the first bobbin 22. Thereby, the shape of the groove 24 changes along the bobbin circumference and becomes progressively flatter. On its mantle surface the first bobbin 22 comprises a flattened portion 23 above the deepest portions of the groove 24. The configuration of the second bobbin 32 is a symmetrically mirrored configuration of the first bobbin 22. The groove 24 terminates at one end into a chamfered shoulder 27 which constitutes a sharply reduced silhouette. The progressively flattening shape of the groove 24 is suitable to deform, as the bobbin is rotated, a tube to be provided sufficiently to affect flow through the tube. By way of the chamfered shoulder 27, the groove 24 is configured to permit the flow of through a tube to be effectively blocked. Thus, the chamfered shoulder 27 constitutes a shape suitable to deform a tube to affect and block flow through it.

Both the first bobbin 22 and the second bobbin 32 are rotatably disposed next to each other on the carriage 46 such that the mantles of each bobbin face each other. The carriage 46 constitutes a common support for the bobbins. The surface portions of the grooves 24 constitute boundaries of a free space through which a tube may extend. When the flattened portion 23 of the first bobbin 22 and the corresponding flattened portion of the second bobbin 32 are aligned to face each other, as shown in FIG. 4, the flattened portions provide a passage 25 through which a tube to be provided may be inserted into the free space between the bobbins.

The carriage 46 is slidably disposed on a housing 50 of the clamping mechanism. The housing contains further a lead screw 42, a toothed rack 44, tracks 48 and a stepper motor 56. The housing 50 constitutes a frame and is provided to maintain a length of tube (tube not shown in FIG. 4) in a defined spatial relationship relative to the clamping mechanism. This allows to ensure that a length of tube is available that corresponds at least to the full range of translational movement of the carriage 46 and, thus, the translational range of the bobbins. This facilitates unimpeded operation of the clamping device.

Figure 5:
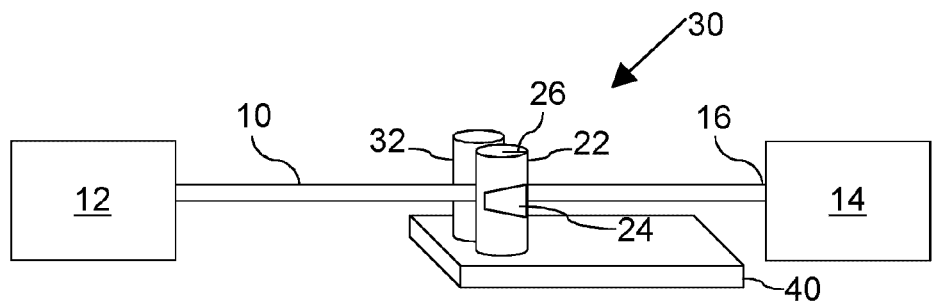
FIGS. 5 to 7 show steps of a sequence of a clamping mechanism in accordance with an exemplary embodiment of the invention in use.
Figure 6:
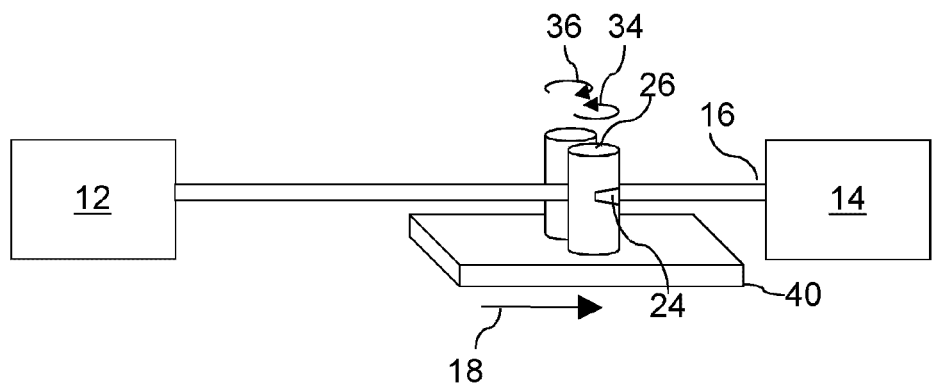
Figure 7:
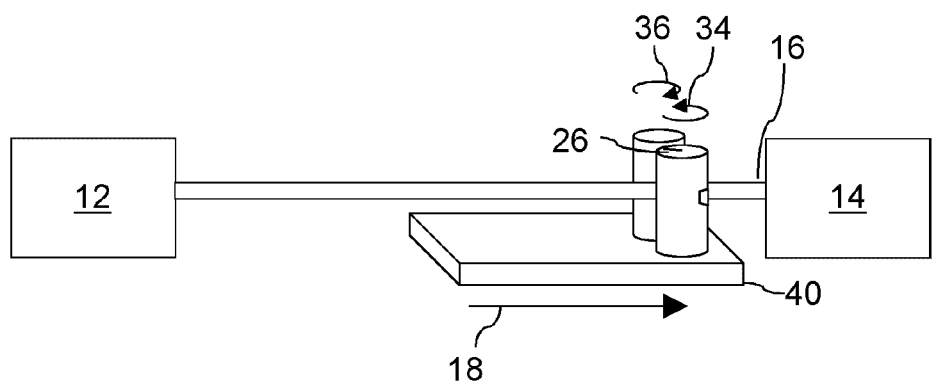

The housing 50 comprises a cut-out 52 for locating a tube (such a tube 10 shown in FIGS. 5 to 7). The cut-out 52 is approximately aligned in height with the grooves 24 such that a tube located in the cut-out 52 is not subject to undue bending forces within the device.

The lead screw 42 constitutes a driver and is configured to effect rotation of the bobbins. The lead screw 42 is actuatable by the stepper motor 56 and coupled with a gear mechanism beneath the bobbins (the gear mechanism is not visible in FIG. 4), whereby rotation of the lead screw 42 is translated in a synchronous counter-rotation of the two bobbins.

The toothed rack 44 comprises a toothed arrangement for engagement with a gear (gears not shown in FIG. 4) associated with each bobbin. As a bobbin rotates, the gear moves along the toothed rack 44 and causes the groove 24 of each bobbin to roll along a tube 10. It will be understood that, as the grooves 24 of the two bobbins simultaneously roll along a tube, the free space between the grooves 24 is altered corresponding to the changing shape of the grooves 24. I.e., the free space increases to reduce a restriction, or the free space decreases to increase a restriction.

In embodiments, the lead screw 42 engages the carriage 46 on which the bobbins are rotatably disposed, and the toothed rack 44 is engaged with a gear associated with each bobbin. As the carriage 46 is moved along the housing 50 by the lead screw 42, the bobbins are pulled along with the carriage 46, and due to the engagement between the toothed rack 44 and the bobbin gears, the bobbins contemporaneously rotate. Thereby, the bobbins are configured to engage the tube in a synchronised manner.

The housing 50 and the carriage 46 comprise corresponding tracks 48 to guide the carriage 46 along the housing. The lead screw 42 and the toothed rack 44 extend along a line parallel to the tube to be provided, to facilitate its engagement with the bobbins.

Each bobbin is provided with a button 54 constituting an actuator of a quick-release function. Actuation of the button 54 disengages the bobbins from the carriage 46. This allows the bobbins to be removed manually without difficulty and without risking damaging the mechanism. This may be used, for instance, to be able to remove any restriction in an emergency.

The clamping mechanism comprises an independent power supply, i.e., a power supply that is at least temporarily independent of mains power supply (not shown). The independent power supply may be a medium capable of storing energy. The energy storage medium may be a supercapacitor. The energy storage medium may be a battery. Although intended for mains-powered use within a clinical setting, in the case of power loss, the energy storage medium provides back-up power to carry out an emergency functionality. For instance, the emergency functionality may consist of removing any restriction on the tube 10 by rotating the bobbins to their open position.

Turning to the sequence of steps shown in FIGS. 5 to 7, these show a clamping mechanism 30 in use as an adjustable restriction for the tube 10 between a source 14 and an outlet 12. Although FIGS. 5 to 7 show, for ease of understanding, only selected elements of the clamping mechanism 30, it will be understood that the exemplary embodiment of FIG.

4 may be used. E.g., the tube 10 might be inserted via the passage 25 and located in the cut-out 52 of the housing 50, as depicted in FIG. 4.

In FIG. 5, the first bobbin 22 and the second bobbin 32 are in an open position and the tube 10 is not squeezed. FIG. 5 can be understood to correspond to the configuration shown in FIG. 2A. No flow restriction occurs.

In FIG. 6, the first bobbin 22 and the second bobbin 32 have been counter-rotated, as indicated by a first arrow 34 for the first bobbin 22 and by a second arrow 36 for the second bobbin 32. In contrast to FIG. 3, the bobbins are also translated by an amount proportionate to the degree of rotation along the frame 40. The translational movement of the bobbins along the frame 40 is indicated by an arrow 18. Although the driver is not shown in FIG. 6, it will be understood that the rotation of each bobbin may be effected by a lead screw driving the carriage 46 and that each bobbin may be coupled via a gear to a toothed rack of the frame 40, and thus each bobbin rotates as the carriage 46 is moved. In FIG. 6, the free space between the grooves is reduced relative to FIG. 5 such that flow through the tube is restricted, in principle corresponding to the configuration shown in FIG. 2B. For instance, the flow through the tube may be restricted to no more than 2 lpm.

In FIG. 7, the first bobbin 22 and the second bobbin 32 are rotated to the distal end of the rack 40, at which the grooves 24 are so shallow, for instance by way of a chamfered shoulder 27 as shown in FIG. 4, as to completely occlude the tube 10. Flow through the tube 10 is blocked, or at least practically reduced to an extent that the flow rate of fluid through the tube 10 is negligibly low.

In the steps indicated in FIGS. 6 and 7, the grip of the grooves on the tube could be considerable and so, in the absence of the translational movement of the bobbins relative to the tube, contemporaneous gripping and rotating would risk putting a strain on the connection 16. By way of the translatably disposed bobbins, a friction-reducing arrangement is provided. The pulling effect on the tube 10 is reduced, and practically eliminated, because instead of pulling the tube relative to stationary bobbins, the bobbins roll along the tube while gradually restricting the flow.

The use of a lead screw as driver and the use of toothed gears as a bobbin-frame coupling mechanism is exemplary. The coupling mechanism facilitates the synchronous movement of the bobbins. Other mechanism may be used. For instance, a lead screw may turn to rotate the bobbins and may also transport a carriage carrying the bobbins. The bobbins may be driven independently, for instance by separate lead screws or individual motorisation.

Comparing FIGS. 6 and 7, it will be understood that a different degree of rotation of the bobbins corresponds to a different amount of squeezing of the tube 10 and, thus, to a correspondingly smaller or greater restriction of flow through the tube 10. A controller may be configured with a mapping functionality that permits the controller, for a given setup, to define a relationship between the degree of rotation or groove geometry and the effective flow restriction. This facilitates setting of a particular restriction level.

The present clamping mechanism may be used as an adjustable restriction in a control system as described in United Kingdom patent application number GB1520364.9 by the present applicant.

A control system as described in GB1520364.9 is provided to restrict the flow rate of blood in a blood line in which blood is permitted to flow from an inlet towards an outlet. The control system comprises a first flow sensor configured to determine a first flow value indicative of the flow rate in the blood line, a controller configured to process the first flow value, and an adjustable restriction responsive to the controller, wherein the adjustable restriction is configured to reduce the flow rate in the blood line to maintain a flow rate that does not exceed a restriction threshold.

An adjustable restriction may be constituted by a clamping mechanism described in the present specification.

An adjustable restriction that is responsive to a flow sensor can be regarded as a closed loop control. This provides a mechanism to maintain a pre-determined flow threshold regardless of the type of tubing or the type of restriction employed. The closed loop control reduces, and practically avoids, the risk of restricting a blood line more than intended.

Furthermore, the restriction threshold may be set to a low flow level while ensuring that a minimum flow rate is maintained. This allows low restriction thresholds to be maintained in situations in which flow must not be stopped entirely.

The control system may be configured to determine whether or not the first flow value exceeds the restriction threshold by a pre-determined margin, and may be configured to effect an adjustment of the adjustable restriction to maintain the flow rate below the restriction threshold.

In embodiments, the tube 10 constitutes a blood line.

In embodiments, the blood line comprises a venous line for draining blood into a reservoir. The first flow sensor is configured to determine the first flow value indicative of the venous flow rate and the adjustable restriction is configured to maintain the venous flow rate in the venous line.

Such control systems may be used in an extracorporeal venous line of a perfusion system. The venous line allows blood from a patient to be drained into an extracorporeal venous reservoir.

By restricting the flow rate through the venous line, the amount of blood circulating in a patient may be increased.

This functionality provides options for a better control of the extracorporeal blood supply during the end phases, or "weaning", of perfusion support. The end phases may be split into (a) initiating the end of the extracorporeal perfusion support, (b) maintaining a gradually reduced extracorporeal perfusion support to allow heart performance to be monitored, (c) if required, resuming extracorporeal perfusion, and (d) when possible, completely ceasing extracorporeal perfusion and letting the heart take over circulation.

The adjustable restriction may be positioned at an inlet of the reservoir and/or upstream of an inlet of the reservoir (in the venous line). The adjustable restriction may be configured for attachment at an inlet of the reservoir or be integral with the reservoir. The adjustable restriction and the flow sensor may be provided as a single, integrated module. The provision of flow sensor and adjustable restriction as a single module may facilitate installation in a perfusion system.

In embodiments, the control system is provided for use in a perfusion system comprising a pump to circulate blood from the reservoir via a main blood line towards an outlet. The pump is responsive to the controller, and the controller is configured to modulate operation of the pump to maintain the throughput towards the outlet at a pre-determined output flow rate. The control system further comprises a second flow sensor configured to determine a second flow value indicative of the flow rate in the main blood line, and the controller is configured to determine a difference between the second flow value and the pre-determined output flow rate, and to adjust pump parameters to reduce the difference.

The pump of a perfusion system may be any suitable pump, such as a peristaltic pump or roller pump, or a centrifugal pump. The pump draws blood from the reservoir and brings it to a line pressure and flow rate for subsequent administration to a patient. The blood is typically pumped through an oxygenator. Other conditions, e.g. temperature, may also be adjusted prior to administration to the patient.

The second flow sensor may be a separate sensor, e.g., downstream of the pump or downstream of the oxygenator. This allows the actual flow rate to be determined, taking into account any losses that may occur between the pump and the second flow sensor.

The second flow sensor may be constituted by an arrangement deriving the second flow value from the operational parameters of the pump. E.g., for a given setup, (e.g., pump speed, tube diameter, etc.), the revolutions, or strokes, per minute can be correlated with the output flow rate.

A single controller may be provided both to control the adjustable restriction in response to the first flow value and to control the pump parameters. Alternatively, individual controllers may be provided, one each to control the adjustable restriction and to control the pump parameters.

In embodiments, the control system is configured to allow the restriction threshold and the pre-determined output flow rate to be set independently.

The output flow rate (e.g., pump performance) and the restriction threshold (e.g., the adjustable restriction) may be controlled independently.

This provides a mechanism to better control the amount of blood in the vascular system depending on the requirements of a patient. As a simplified explanation, during the end phase of extracorporeal perfusion, blood is transferred from the venous reservoir into the patient. This may be referred to as "filling" the vascular system, whereas by "filling", it is meant that the amount of blood in the vascular system is gradually increased, while correspondingly less blood is held in the extracorporeal venous reservoir.

The restriction threshold and the pre-determined output flow rate may each be set via a respective input interface. This allows a clinician to set a restriction threshold but not alter the pre-determined output flow rate. For instance, the restriction threshold may be set to 2 lpm, and no pre-determined output flow rate may be set. Thus, the output flow rate may be governed by other clinical considerations. Likewise, a clinician may set a pre-determined output flow rate without altering the restriction threshold.

The restriction threshold and/or the pre-determined output flow rate may be changed incrementally (e.g., "Increase by 0.1 lpm" or "Reduce by 0.1 lpm"), e.g., via a user interface with "up" and "down" buttons.

The pre-determined output flow rate may be set according to clinical requirements. The output flow rate may be set via an input interface. For instance, the pre-determined output flow rate may be set to 3 lpm. If the second flow value, as measured by the second flow sensor, is above the output flow rate, the controller is configured to reduce the pump performance, until blood is pumped from the reservoir at a second flow value of 3 lpm. If the second flow value is below the output flow rate, the controller may increase the pump performance until the second flow value is determined as 3 lpm.

In embodiments, the controller is configured to adjust the pre-determined output flow rate relative to the restriction threshold.

In embodiments, the controller is configured to maintain the pre-determined output flow rate above the restriction threshold, at the restriction threshold, or below the restriction threshold.

The pre-determined output flow rate may match the restriction threshold (e.g., both may be set to 3 lpm). The pre-determined output flow rate may be set as an offset relative to the restriction threshold, e.g., 0.5 lpm above the restriction threshold. The pre-determined output flow rate may be set at a percentage relative to the restriction threshold.

If the output flow rate is set higher than the restriction threshold, blood can be supplied to a patient at a higher rate than it is allowed to be drained via the venous line. This allows the vascular system to be filled. I.e., this allows the amount of blood in the vascular system of a patient to be increased.

If the output flow rate matches the restriction threshold, blood is supplied to a patient at the same rate as it is allowed to be drained. This maintains a steady amount of blood in the vascular system. Thus, extracorporeal perfusion may circulate blood at a lower rate, whereas the heart takes over the circulation of the blood in the vascular system. For instance, while the heart is stopped during a medical procedure, extracorporeal perfusion may supply and drain blood at a rate of 5 lpm. The invention allows blood to be supplied, e.g., an output flow rate of 2 lpm, and drained at no more than 2 lpm, as set by a restriction threshold.

The provision of a steady blood supply and drainage allows the heart performance to be monitored under better defined conditions.

If the output flow rate is set lower than the restriction threshold, blood is supplied to a patient at a lower rate than it is allowed to be drained. This will decrease the amount of blood in the vascular system of a patient. This reduces the load on the heart and may be appropriate during a complication.

In embodiments, the controller is configured to adjust the restriction threshold and the output flow rate synchronously.

For instance, to promote a gradual increase in heart activity, the output flow rate and the restriction threshold may be reduced synchronously. E.g., both may be reduced from 2 lpm to 1 lpm. This provides a balanced blood supply and blood removal.

The system may be configured to receive a single input value (e.g., 2 lpm) for both the output flow rate (e.g., pump performance) and the restriction threshold (e.g., the adjustable restriction). The system may be configured to receive an input value for one of the output flow rate and the restriction threshold, and the other of the output flow rate and the restriction threshold may be adjusted correspondingly.

The output flow rate and the restriction threshold may be matched, or may differ. For instance, the output flow rate may be set to 110% of the restriction threshold. In that case, if an adjustment to the restriction threshold is made, this may cause the controller to correspondingly adjust the output flow rate (and pump performance) to 110% of the previous output flow rate.

The synchronous adjustment may be bi-directional. By "bi-directional", it is meant that the output flow rate and the restriction threshold may both be increased or both be decreased. The effect is that the extracorporeal blood supply is increased (when the output flow rate and the restriction threshold are raised) and less strain is put on the heart, or decreased, respectively, such that more heart activity is encouraged.

In embodiments, the control system is configured to receive as an input a pressure value indicative of the physiological blood pressure of a patient, and to adjust the output flow rate in response to the physiological blood pressure.

In embodiments, the control system is configured to receive as an input a pressure value indicative of the physiological blood pressure of a patient, and to adjust the restriction threshold in response to the physiological blood pressure.

In embodiments, the pressure value comprises the Central Venous Pressure (CVP) and/or the Pulmonary Artery Diastolic Pressure (PAD). For ease of reference, CVP characterises the right-side heart function, and PAD characterises the left-side heart function. Under normal physiological conditions, PAD is expected to be higher than CVP.

The pressure value may be measured using established pressure sensors, such as a Swan-Ganz catheter. Such pressure sensors are used routinely during heart surgery. Pressure values may be provided as an input to the controller.

The relationship between the amount of blood in circulation and the pressure values in the vascular system is complex. As the amount of blood in the patient changes, so does the blood pressure in the vascular system and in the heart chambers of the patient. The efficiency of the heart may be described by Starling's Law, which describes the relationship between the stroke volume of the heart and the pre-loaded volume of blood in a heart chamber, which depends on the amount of blood in the vascular system. As a simplified explanation, increasing the amount of blood in circulation results in an increased volume of blood pumped per heartbeat, but only up to a limit. Above the limit, further increasing the amount of blood in circulation decreases the volume of blood pumped per heartbeat. The limit differs among patients but is typically in the region of between 10 to 15 mmHg (1 mmHg=133.322 Pa) for the central venous pressure (CVP) and in the region of 19 to 20 mmHg for the pulmonary artery diastolic pressure (PAD).

For instance, the output flow rate may be maintained higher than the restriction threshold. Initially, only the restriction threshold may be set, e.g., to 2 lpm, whereas the output flow rate may not be adjusted. This means that blood will continue to be supplied towards the patient at a regular, unrestricted level about 5 lpm, but is only allowed to drain at about 2 lpm. This increases the filling rate (i.e., more blood is supplied to the patient than is allowed to leave the patient). As the vascular system is filled, a vascular pressure value (e.g., the central venous pressure, CVP) may also increase. The output flow rate may be maintained above the restriction threshold until the vascular pressure value reaches a pressure threshold. For instance, the filling may be stopped when a pressure threshold of 20 mmHg (PAD) is reached.

Distinguishing between left-side and right-side pressures provides a better control of filling when filling volumes are large relative to the patient. For instance, a translocated volume of 300 ml blood may be a relatively small amount for an adult, and may be considered safe enough as a first-level estimate. In contrast, in paediatric surgery, it may not be considered safe to translocate 300 ml blood. By providing a mechanism that fills the vascular system based on a pressure threshold, a safe volume of blood can be translocated without having to estimate the volume of blood in advance.

When the vascular pressure approximates or reaches the pressure threshold, the difference between the output flow rate and the restriction threshold may be reduced until they match. For instance, the output flow rate may be raised thereby to reduce the restriction, and/or the restriction threshold may be increased, until both are at the same level. This will result in the blood supply and drainage being in balance at the pressure threshold.

The filling procedure may be automated by setting a pressure threshold. The controller may modulate the restriction threshold and/or the output flow rate (and thereby, cause the adjustable restriction and/or the pump performance to be adjusted) until the pressure threshold is reached. The procedure may be semi-automated, e.g., by providing an indication to a clinician how, for a set pressure threshold, the restriction and/or the output flow rate should be adjusted, but leaving the actual control over when the adjustment is initiated to the judgment of the clinician.

Furthermore, the control system may be configured to alter the restriction threshold dynamically in response to the pressure value. For instance, while the pressure value is low (or close to zero), the restriction threshold may be very low, allowing the vascular system to be filled quicker. In other words, the ratio of the output flow rate to the restriction threshold may be larger the greater the difference between the pressure value and the pressure threshold. As the pressure in the vascular system starts to increase or change, the restriction threshold may be reduced, such that ratio of the output flow rate to the restriction threshold decreases. Thereby, the pressure value increases more slowly, which allows more response time to for clinical staff. This provides improved safety while also allowing a high filling rate when this is safe.

The control system may comprise a second pressure threshold or maximum pressure threshold as a safeguard. For instance, once the maximum pressure threshold is reached, the controller may not allow the output flow rate to exceed the restriction threshold. The controller may be configured to increase the restriction threshold to allow more blood to be drained via the venous line.

In embodiments, the control system comprises a processor and software instructions implemented by the processor permitting it to control the adjustable restriction in response to the first flow value.

Likewise, the software instructions may permit the processor to control any of the other components of the control system.

The present invention may be used in other scenarios in which a high precision modulation of a flow rate or flow threshold is desired.

The invention claimed is:

1. A perfusion system comprising:
   an extracorporeal venous reservoir;
   a flexible tube configured as a venous blood line for allowing blood from a patient to be drained through the flexible tube into the extracorporeal venous reservoir;
   a pump configured to circulate blood from the extracorporeal venous reservoir via a main blood line towards an outlet;
   two rotatable bobbins, each bobbin comprising a tube-engaging surface portion, wherein the tube-engaging surface portions define boundaries of a free space between the bobbins through which the flexible tube may extend, and wherein at least one tube-engaging surface portion has a shape that changes around at least part of a circumference of the bobbin, such that axial rotation of the bobbins rolls the bobbins along the flexible tube and modifies the free space to allow the flexible tube provided in the free space to be squeezed by an amount dependent on the rotation of the bobbins, so as to deform the tube sufficiently to affect flow through the tube;
   a flow sensor configured to determine a flow value indicative of a flow rate through the flexible tube; and a controller configured to process the flow value and programmed with control logic configured to:
  generate, for a given setup of the tube and the bobbins, a mapping between a maximum flow rate through the tube and either (i) a degree of bobbin rotation, or (ii) a position along the tube-engaging surface portion;
  receive, as an input, a flow rate restriction threshold;
  convert the flow rate restriction threshold to either (i) an amount of bobbin rotation, or (ii) a position along the tube-engaging surface portion;
  rotate the bobbins according to either (i) the amount of bobbin rotation, or (ii) the position along the tube-engaging surface portion; and
  switch to a closed-loop control in which the flow value from the flow sensor is used to adjust the amount of bobbin rotation to maintain a flow rate that does not exceed the flow rate restriction threshold.

2. The perfusion system according to claim 1, further comprising a translatable carrier on which the bobbins are disposed to allow the bobbins to move along the tube as the bobbins are rotated.

3. The perfusion system according to claim 1, wherein the bobbins are configured to engage the tube in a synchronized manner.

4. The perfusion system according to claim 1, further comprising a driver configured to effect synchronized rotation of both bobbins.

5. The perfusion system according to claim 2, comprising a frame on which the carrier is translatable relative to the tube to be provided.

6. The perfusion system according to claim 5, further comprising a bobbin-frame coupling mechanism configured to couple rotation of a bobbin with a movement of the bobbin along the frame.

7. The perfusion system according to claim 1, further comprising a backup power source.

8. The perfusion system according to claim 2, further comprising a quick-release feature causing, upon its actuation, the bobbins to disengage from the carrier.

9. A clamping mechanism for clamping a flexible tube to be provided, the clamping mechanism comprising:
  two rotatable bobbins, each bobbin comprising a tube-engaging surface portion, wherein the tube-engaging surface portions define boundaries of a free space between the bobbins through which a tube may extend, and wherein at least one tube-engaging surface portion has a shape that alters around at least part of a circumference of the bobbin, such that axial rotation of the bobbins alters the free space available to accommodate a tube, and
  a translatable carrier on which the bobbins are disposed to allow the bobbins to move along the tube as the bobbins are rotated,
  wherein the clamping mechanism comprises a quick-release feature, wherein each bobbin comprises an actuator of the quick-release feature causing upon its actuation its bobbin to disengage from the carrier.

* * * * *